(12) United States Patent
Schroeppel et al.

(10) Patent No.: US 6,366,808 B1
(45) Date of Patent: Apr. 2, 2002

(54) IMPLANTABLE DEVICE AND METHOD FOR THE ELECTRICAL TREATMENT OF CANCER

(76) Inventors: Edward A. Schroeppel, 215 Dewberry Dr., Lake Jackson, TX (US) 77566; Mark W. Kroll, 493 Sinaloa Rd., Simi Valley, CA (US) 93065

( * ) Notice: Subject to any disclaimer, the term of this patent is extended or adjusted under 35 U.S.C. 154(b) by 0 days.

(21) Appl. No.: 09/524,405

(22) Filed: Mar. 13, 2000

(51) Int. Cl.⁷ ................................................ A61N 1/36
(52) U.S. Cl. ............................................. 607/2; 607/72
(58) Field of Search ............................... 607/66, 67, 68, 607/69, 70, 71, 72, 73, 74, 75, 76, 50, 51, 52, 2

(56) References Cited

U.S. PATENT DOCUMENTS

| | | | |
|---|---|---|---|
| 4,026,304 A | * | 5/1977 | Levy |
| 4,289,135 A | | 9/1981 | Nordenstrom et al. |
| 4,572,214 A | | 2/1986 | Nordenstrom et al. |
| 4,679,561 A | | 7/1987 | Doss |
| 4,919,138 A | | 4/1990 | Nordenstrom |
| 4,974,595 A | | 12/1990 | Nordenstrom |
| 5,098,843 A | | 3/1992 | Calvin |
| 5,501,662 A | | 3/1996 | Hofmann |
| 5,584,872 A | | 12/1996 | LaFontaine et al. |
| 5,630,426 A | | 5/1997 | Eggers et al. |
| 5,820,548 A | | 11/1998 | Sieben et al. |

OTHER PUBLICATIONS

Reis A, Henninger T. Zerstorung maligner Wachstumsenergie durch anodische Oxydation. Kim Wochenschrift 1951; _: 39.

Nordenstrom B. Preliminary clinical trials of electrophoretic ionization in the treatment of malignant tumors. IRCS Med Sc 1978; 6: 537.

Schanble MK, Mutaz HB, Gallick HD. Inbitition of experimental tumor growth in hamsters by small direct currents. Arch Pathol Lab Med 1977; 101: 294.

Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.

Nordenstrom BEW. Biologically closed electric circuits: clinical, experimental and theoretical evidence for an additional circulatory system. Stockholm: Nordic Medical Publications, 1983.

Nordenstrom B. Biologically closed electric circuits: activation of vascular interstitial closed electric circuits for treatment of inoperable cancer. Journal of Bioelectricity 1984; 3(162): 137–153.

Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51–53.

Mir LM, Orlowski S, Belehradek Jr J, Paoletti C. Electrochemotherapy potentiation of antitumour effect of bleomycin by local electric pulses. Eur J Cancer 1991; 27:68–72.

Wolf B, Kraus M, and Sieben U, "Potential of microsensor–based feedback bioactuators for biophysical cancer treatment," Biosensors and Bioelectronics, vol. 12, No. 4, pp 301–309, 1997.

Kirsch DL, Lerner FN. Electromedicine: the other side of physiology. In: Innovations in pain management: a practical guide for clinicians. Winter Park, FL: GR Press, 1995.

Li K, Xin Y, Gu Y, Xu B, Fan D. Ni B. Effects of direct current on dog liver: possible mechanisms for tumor electrochemical treatment . Bioelectromagnetics 1997; 18: 2–7.

(List continued on next page.)

Primary Examiner—Scott M. Getzow

(57) ABSTRACT

An implantable electrical method and apparatus for the treatment of cancer tumors based on the usage of various levels of electrical fields and current to assist in specific ways to reduce tumor size.

22 Claims, 16 Drawing Sheets

OTHER PUBLICATIONS

Berendson J. Simonsson D. Electrochemical aspects of treatment of tissue with direct current. Eur J Surg 1994: Suppl 574: 111–115.

Song Y, Li C, Li Y, Song Q. Chang B, Song L. Liu C. Wang T. Electrochemical therapy in the treatment of malignant tumors on the body surface. Eur J Surg 1994; Suppl 574: 41–43.

Matsushima Y, Takahashi E, Hagiwara K, Konaka C, Miura H, Kato H, Koshiishi Y. Clinical and experimental studies of anti–tumoural effects of electrochemical therapy (ECT) alone or in combination with chemotherapy. Eur J Surg 1994; Suppl 574: 59–67.

Xin Y, Xue F, Ge B, Zhao F, Shi B, Zhang W. Electrochemical treatment of lung cancer. Bioelectromagnetics 1997; 18: 8–13.

Nordenstrom BEW. Electrochemical treatment of cancer. I: variable response to anodic and cathodic fields. Am J Clin Oncol (CCT) 1989; 12(6): 530–536.

Nordenstrom BEW. Survey of mechanisms in electrochemical treatment (ECT) of cancer. Eur J Surg 1994: Suppl 574: 93–109.

Chen B, Xie Z, Zhu F. Experimental study on electrochemical treatment of cancer in mice. Eur J Surg 1994; Suppl 574: 75–77.

Chou C, McDougall JA, Ahn C, Vora N. Electrochemical treatment of mouse and rat fibrosarcomas with direct current. Bioelectromagnetics 1997; 18: 14–24.

Nordenstrom BEW, Eksborg, S., Beving, H. Electrochemical treatment of cancer. II: effect of electrophoretic influence on adriamycin. Am J Clin Oncol (CCT)1990; 13(1): 75–88.

Xin, Y. Organisation and spread of electrochemical therapy (ECT) in China. Eur J Surg 1994; Suppl 577: 25–30.

Quan, K. Analysis of the clinical effectiveness of 144 cases of soft tissue and superficial malignant tumors treated with electrochemical therapy. Eur J Surg 1994; Suppl 574: 37–40.

Wang, H. Electrochemical therapy of 74 cases of liver cancer. Eur J Surg 1994; Suppl 574: 55–57.

Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79–81.

Yokoyama, M., Itaoka, T., Nakajima, H., Ikeda, T., Ishikura, T., Nitta, S. [The use of direct current in the local destruction of cancer tissues]. Gan To Kagaku Ryoho 1989 Apr; 16(4 Pt 2–2): 1412–1417.

Okino, M. and Mohri, H. Effects of high voltage electrical impulse and an anti–cancer drug on growing tumors. Japanese Journal of Cancer Research, vol. 78, pp. 1319–1321, 1987.

Orlowski, S., Belehradek, J.J., Paoletti,C. and Mir, L.M. "Transient electropermeabilization of cells in culture increase of the cytotoxicity of anti–cancer drugs", Biochem, vol. 37, No. 24, pp. 4727–4733, 1988.

Belahradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155–163, 1994.

Hofmann, G.A., Dev. S.B., Dimmer, S. and Nanda, G.S., "Electroporation Therapy: A new approach to the treatment of head and neck cancer, IEEE Transactions On Biomedical Engineering", vol. 46, No. 6, pp. 752–759, 1999.

Schechter, DC. "Containment of Tumors Through Electricity." PACE 1979. vol. 2, pp 100–114.

Sersa, et al. Improvement of Combined modality therapy with cisplatin and radiation using electroporation of tumors. Int J. Radiation Oncology Biol. Phys. vol. 46, No. 4:1037–1041. (2000).

Hofmann, Dev, Nanda, and Rabussay. electroporation therapy of solid tumors. Critical Reviews in therapeutic Drug Carrier Systems 16(6):523–569 (1999).

Samuelsson, Harnek, Ewers, Jonsson. Electrochemical and megavolt treatment of rat tumors. Eur J Surg Suppl 574:69–70. (1994).

Habal and Schauble. An implantable DC power unit for control of experimental tumor growth in hamsters. Medical Instrumentation 7 No. 5: 305–306. (1973).

Semrov and Miklacic. Calculation of the electrical parameters inn electrochemistry of solid tumors in mice. Comp Biol Med 28:439–448. (2000).

Turler, Schaefer, et al. Local treatment of hepatic metastases with low level direct electrical current: experimental results. Scand J Gastroenterol. 3:322–328. (2000).

\* cited by examiner

IMPLANTABLE DEVICE AND METHOD FOR THE ELECTRICAL TREATMENT OF CANCER

This application is related to The Provisional application filed on Apr. 9, 1999, Ser. No. 60/128,505, entitled "Implantable System for the Electrical Treatment of Cancer.

BACKGROUND OF THE INVENTION

Cancer is one of the major causes of hospitalization and death worldwide. Many of the therapies applied to cancer treatment are either ineffective or not well-tolerated by the patient. A promising approach that is little known but which has been successfully applied in Sweden, China, Germany, and Japan involves the electrical stimulation of a malignant tumor using direct current electricity. This has become known as electrochemical treatment (ECT). The clinical results have been obtained by applying electrical current via electrodes inserted percutaneously into the tumor. The treatment lasts for several hours during one or more sessions and can be used either alone or in conjunction with other therapy such as chemotherapy or radiation therapy. The therapy is well-tolerated in almost all patients.

This method is not to be confused with the electroporation technique which uses high voltages (~1 kV) with very short pulses.

The present invention overcomes some of the disadvantages of the ECT method mentioned above. It involves an implantable device consisting of a generator and one or more wires containing one or more electrodes. The electrodes are implanted in or near the tumor and the generator is implanted subcutaneously as close to the tumor as practical. The generator is powered either by an internal battery or via energy coupled to it from a source external to the body. The implantation is typically performed under local anesthesia and the device is left implanted for a period of months. Implantation permits electric current to be applied at lower levels for longer time periods, thus overcoming some of the drawbacks of the method above.

The nature of the implant results in some key differences from cardiac pacemaker design allowing for less stringent requirements on package and wire longevity. Other differences are manifested in the anchoring of the electrodes and in functions of the generator. The device complexity can range from very basic to sophisticated, including programmability of multiple parameters, patient alert mechanisms, sensors, and telemetry of information. The system may also include an external instrument for programming, telemetry reception, and data analysis. In one embodiment, chemotherapy drugs are infused from the generator in addition to the electrical stimulation.

Disease Prevalence

Cancer malignancies result in approximately 6,000,000 deaths worldwide each year. Of these, 538,000 were in the United States in 1995, representing over 23% of the total deaths in the United States. This number is up from 1970, when 331,000 deaths occurred. The estimated number of new cases in the United States in 1997 was 1,382,000. 40% of Americans will eventually be stricken with the disease and more than 1 in 5 will die from it. The percentage is increasing at about 1 % per year and cancer deaths will soon outstrip deaths from heart disease. Much of the medical care cost from cancer results from hospitalization. In 1994 there were 1,226,000 hospital discharges in the United States related to cancer treatment.

The cost of cancer in terms of both human suffering and expenditures is staggering.

Effective treatment methods which also result in fewer days of hospital care are desperately needed.

Cancer Treatment Methods

Primary treatment methods used in cancer therapy include surgery, radiation therapy, chemotherapy, hormone therapy and many others including bone marrow replacement, biological response modifiers, gene therapy, and diet. Therapy often consists of combinations of treatment methods. It is well known that these methods may result in sickness, pain, disfigurement, depression, spread of the cancer, and ineffectiveness. Despite recent to announcements of potential pharmaceutical "cures," these may work well in animals and in humans in certain cases, but researchers are cautious in overstating their effectiveness.

The therapy made possible by the novel devices described in this report is seen to have many benefits, including:

They may be used for either the primary treatment of neoplasms or during regression.

They require a single implant procedure, not repeated applications of invasive therapy, an important consideration in seriously ill individuals.

This and the lack of leads passing through the skin reduce the chance of infection.

Slow application of lower levels of current is preferable to larger quantities of charge over a short period of time. Extended use may prevent future metastases.

They have no disabling side effects as are found with chemotherapy or radiation therapy.

Their use is suitable in conjunction with other therapies.

Minimal hospital stays are required.

The device cost and complexity are low relative to pacemakers.

Since the therapy delivered by these implantable devices is based on the theory and clinical experience of B. E. Nordenstrom and others, their work and conclusions are first summarized below.

Early and Related Studies of Electrical Current in Tumors

Reis and Henninger caused regression of Jensen sarcomas in rats in 1951 using direct current and applied the technique to one patient with vulvar cancer. Lung tumors were first treated with direct current by Nordenstrom as reported in a 1978 publication. Experiments using small amounts of direct current to inhibit tumor growth were performed by Schanble et al. as well as others. Srinivasan et al. mention the possibility of controlling malignant tumor growth by direct current. Direct current has been used to coagulate blood in vessels leading to tumors and others (circa 1980) experimented with electrolytic destruction of tissue in animals using direct current (See Nordenstrom 1983). Mir et al. successfully treated tumors with bleomycin and eight pulses of 100 microsecond width at 1 Hz with a field intensity of 1500 V/cm. They concluded that the minimum intensity required was 1100–1200 V/cm.

The Work of B. E. Nordenstrom

Bjorn Nordenstrom of Sweden, a pioneer and inventor in percutaneous needle biopsy and former Chairman of the Nobel Assembly, performed extensive research in electromedicine, developed a theory on the nature of bioelectricity and the healing process, and treated cancer in his patients as clinical proof of his theories. He called his model of biological control systems "biologically closed electric circuits" (BCEC) and sought to explain structural development in tissue injury and particularly around cancers. He found that treatment of cancer with DC electrodes changes the microenvironment of the cancer cells by electrophoresis of water and fat and electroosmosis of water. The therapy that is based upon this principle is called "electrochemical treatment" (ECT). Direct current ionizes tissue (as does ionizing radiation). Ionization of tissue via direct electrodes affects normal and malignant tissues differently. Low energy levels build up the therapeutic dose of energy from the inside of the tumor.

Tumor cells are more sensitive to changes in their microenvironment than are normal cells. The effect of the application of direct current to cells with platinum electrodes has been summarized succinctly by Li et al.:

Water migrates from the anode to the cathode while fat moves in the opposite direction (this migration causes local hydration around the cathode and dehydration around the anode).

The tissue becomes strongly acidic at the anode and strongly alkaline at the cathode.

The distributions of macro- and microelements in the tumor tissue are changed.

Protein is denatured in the electrochemical process (hemoglobin is transformed into acid hemin around the anode and alkaline hemin around the cathode).

Chlorine, which is a strong oxidant, is liberated at the anode, whereas hydrogen, which produced local cavitation in the tissue, is liberated at the cathode.

By means of DC delivering adequate electric charge, a series of biological and electrochemical reactions take place in tissue. The cell metabolism and its existing environment are severely disturbed. Both normal and tumor cells are destroyed rapidly and completely in this altered environment.

Berendson et al. believe that the toxic properties of the chlorine close to the anode and of the hydrogen chloride within a broader zone may be enough to explain the clinical effects of ECT and that the liberated hydrogen ions determine the extension of the locally destroyed zone around the anode. Several researchers have also observed that destruction occurs around both anode and cathode (Song et al., Matsushima et al., and Xin et al.) as well as within the electric field established between them. (In early works Nordenstrom cautions against making the center of the tumor the cathode as it will cause concentration of the acidity at the wrong location but later reports that, in some cases, better results were achieved with the cathode at the tumor.) Subsequent work in Asia found an advantage in locating both electrodes within the tumor (Xin, 1997). Nordenstrom believed that the electroosmotic transport of water compresses capillaries and was seen to block large pulmonary arteries in dog experiments. He points out that a sufficiently long interval of vascular obstruction will seriously interfere with the living conditions of the tissues. Thus, primary tumor destruction is obtained, along with a change in surrounding conditions that prevent the tumor from living. ECT is also believed to enhance the immune system of the patient (Chen et al., Chou et al). In studies conducted in mice there was infiltration of lymphocytes in tumor tissue six days after treatment. Leukocytes have a negative surface charge and are known to be sensitive to low voltage changes and changes in pH and ion strength. At an electrode voltage as low as 100 mV leukocytes concentrated at the anode. Many leukocytes can be attracted to the anode at relatively low voltages but are massively destroyed in the anodic field at 10 V. Nordenstrom recognized that electrophoretic movements will take place at low voltages and current densities and he discussed possible tissue changes with, for example, 10V and 1 to 2 microamperes applied for 30 days. He wrote " . . . it seems likely that DC treatment should be most beneficial when the technique approaches the mechanisms of closed circuit transport in spontaneous healing. This consideration implies the use of energies perhaps in the range of a few volts and a few microamperes over long time periods." He also deduced that AC potential may be used to heal tissue.

Procedurally, Nordenstrom used electrodes such as those shown in FIG. 1. The electrode is introduced through the chest wall (in the case of lung tumors) into the patient under guidance of biplane fluoroscopy or computed tomography under local anesthesia. In FIG. 1a hooked electrode ends 1 of platinum strings protruding from plastic tube 2 expand within tumor 3 to retain the electrode inside the tumor. In FIG 1b platinum tubes 10–12 provide a larger surface area and can be chosen to correspond with the size of the tumor. Screw 14 is used to obtain biopsy tissue samples. The electrode 13 is shown implanted in tumor 20 in FIG. 1c. Tube 21 is constructed of Teflon®. Alternatively, FIG. 1d shows a tapered platinum tube 30. Screw 31 is used to obtain tissue for biopsy. Area 32 consists of collapsed wings which, as shown in FIG. 1e, expand 40 to stabilize electrode 30 in the tumor. Nordenstrom recognized that a platinum electrode can be improved mechanically by adding iridium. He stated some guidelines for electrode design and implantation. The electrodes should present a large surface area but must be easily introducible without causing too much damage. He recognized in 1994 that regression of cancer can take place both around the anode and the cathode in the tumor. Placement of both electrodes within the tumor can lead to a treatment result comparable with an initially successful surgical removal of a cancer. However, as with surgical removal, metastases may later start growing in the tissue around the former tumor site. Positioning the anode and cathode far enough away from each other will create a distant field effect that should prevent future metastases. Thus, he believed that ECT of "small resectable" cancers might be more efficient than conventional surgical resection. He advised that the use of multiple anodes and cathodes might cause an uneven distribution of current and recommended that electrodes be neither very close nor very far away from one another. The anode should be kept away from direct contact with large blood vessels if using the large currents and voltages used by Nordenstrom (but not with microampere level currents). The cathode may be placed in a blood vessel. Nordenstrom used a catheter that could be percutaneously inserted by Seldinger technique in, for example, a pulmonary artery. Electrodes can theoretically be placed on the skin (although he cautions against this in a later paper) or inserted through a chest wall, via a systemic artery, a systemic vein, a bronchus or in the pleural space. The venous routes and pleural space provide pathways for current that include the lymphatics. Nordenstrom also noted that flushing the anodal electrode with a charged agent such as adriamycin or 5-fluoracil in a manner that causes even distribution of the drug with high concentration can lead to a remarkable regression and palliative effects of even large, incurable cancers. Whether supplied intravenously or orally, these two agents are attracted to the electrode, when given opposite polarity.

Nordenstrom reported treatment of 26 inoperable cancers of the lung in 20 patients starting in 1978 and followed up for 2 to 5 years. Twelve of the cancers were arrested and no fatalities occurred. He observed that in some cases multiple other small metastases in the lung parenchyma, distant from the sites of the electrodes, also appeared to regress after treatment of the larger metastases. He pointed out that the therapy was unoptimized at that time. Radiation treatment of lung tumors is not very effective. A rapid decrease in size of a poorly differentiated tumor after radiation treatment is often accompanied by regrowth of the tumor after a short time. Then the tumor is often more insensitive than previously to any attempts at a repeat course of radiation treatment. He foresaw an advantage of DC current treatment of primary neoplasms in the most surgically inaccessible locations such as the brain, spine, pancreas, liver and prostate and in patients who have been rejected for surgery, radiotherapy or chemotherapy because of poor general condition, cardiorespiratory insufficiency, diabetes mellitus, multiple locations of pulmonary metastases or failing response to chemotherapy. In a later report he cited favorable results with breast and bladder cancer. Also, he treated 14 patients with otherwise incurable cancers with ECT and a chemotherapeutic agent adriamycin infused into the tumor. The principle, already mentioned above, is that an intravascularly electropositive compound will be electrophoretically attracted to a neoplasm electrode given opposite polarity. This treatment was successful on larger tumors than was ECT alone and, in one case, abolished chronic cancer pain. Electrophoresis caused even distribution of the adriamycin throughout the tumor, an effect probably not obtainable with injection.

Recent Human Results in Asia

B. E. Nordenstrom introduced electrochemical therapy in China in 1987 and, partly because of its relationship to traditional Chinese medicine (e. g., acupuncture), its use has been growing in China and interest has spread to Japan and Germany. Xin reported that, by 1994, 4081 malignant tumor cases were treated using ECT in 818 Chinese hospitals including esophageal, breast, skin, thyroid and liver cancers, as well as leg sarcomas. By the end of 1994 more than 6000 cases had been treated. Benign tumors such as heloid, angioma and freckle have also been treated.

Xin et al. published the results of treatment of 386 patients with lung cancer between 1987 and 1989. They found that damage of normal tissue could be eliminated by placing both electrodes into the tumor with anodes in the center and cathodes on the periphery. This has also enhanced the therapeutic effect significantly. They also concluded that the effect of ECT with lower current and longer treatment time is better than high current and shorter time.

Matsushima et al. and Chou et al also placed both electrodes inside the tumor. Matsushima et al studied 26 patients with 27 malignant tumors. The main complications were pain and fever for a few days after treatment. Pain during treatment, especially when the lesion was located in the neck or in soft tissue under the skin, was probably due to sensory nerve stimulation by the direct current. Some lung cancer patients had haemoptysis and pneumothorax.

Song et al. reported the treatment of tumors on the body surface with good results. ECT was found to be suitable for patients at great operative risk, for those who refuse surgery, for those who have not been cured by other means, and for those who have tumor recurrence. They discovered that metastatic enlarged lymph nodes can dissolve when the primary tumor is destroyed by ECT. The method was found to be simple, safe, effective, and readily accepted by patients. ECT can be used in primary as well as metastatic tumors, although the effect is better for primary tumors.

Lao et al. reported on the treatment of 50 cases of liver cancer using ECT. The indications for treatment were: the neoplasm was too large to be easily resected; it was unresectable because of location at the first or second hepatic portals; poor liver fiction secondary to severe cirrhosis making the patient unfit to stand the trauma caused by surgery; cancer infiltration of visceral organs such as the diaphragmatic muscle, peritoneum, or lymph nodes at the hepatic portals.

Quan discussed the ECT treatment of 144 cases of soft tissue and superficial malignant tumors. Short-term effectiveness of treatment was 94.5% for tumors with a diameter of less than 7 cm. and 29.4% for tumors with a diameter of more than 7 cm. He found that the earlier the stage the more effective the treatment and that ECT for malignant melanoma is more effective than chemotherapy and no different in results from surgery. However, ECT eliminated the need for amputation and dysfunction often caused by a too wide surgical excision.

Wang reported on ECT for 74 cases of liver cancer with tumors ranging from 3 to 20 cm. in diameter. The treatments of 3 to 5 hours were repeated 2 to 5 times with 7 to 10 days between each treatment. Total remission rate was 63.51%. Best results were obtained with tumor diameters less than 9 cm. Additional use of cytotoxic drugs and embolization resulted in a 87.5% cure rate.

Song et al. treated 46 patients having thyroid adenoma with ECT and reported a 97.8% cure rate with a single treatment. This represents successful treatment of benign tumors and destruction of precancerous and early malignant changes.

The above reports from China vary in the amount of technical detail presented regarding each study. In general, however, the electrodes were inserted under local anesthetic. The number of electrodes depended upon the tumor size and shape. The goal was to encompass the tumor with the electric field. Xin et al. state that, depending upon tumor composition and location, soft, flexible or hard electrodes with 0.1 cm diameters were used. The anode(s) was(were) placed within the tumor and the cathode(s) was(were) separated by from 1–3 cm. from the anode(s) or by a distance of 2–3 tumor diameters. There were a minimum of 2 electrodes and, at the other extreme, 2 anodes and 4–6 cathodes set up in two groups to establish two electric fields for a tumor of 6 cm. or larger. The treatment time varied from 1.5–5 hours and the number of sessions ranged from 1 to 5, again depending upon tumor size and response to therapy. The voltage used averaged about 8V but ranged from 6 to 15 V. The current ranged from 40–100 mA and the number of coulombs delivered per session ranged from 250 to 2000 C. Quan gives a rule of thumb at 100 C per 1 cm of tumor diameter. Song observed that, at 100 C, the area of destruction around the anode is 0.5–0.6 cm and the area around the cathode is 0.4–0.5 cm. Xin et al. observed some blockage of the heart beat in central lung cancer ECT with currents over 30 mA. Keeping the electrodes more than 3 cm from the heart corrected this effect.

The table below summarizes the types of tumors mentioned as having been treated by the researchers cited above:

| Author | Tumor or Cancer Type |
| --- | --- |
| Xin et al. | Lung, squamous cell, esophageal, parotid, breast, sarcoma of the leg, skin, malignant melanoma, cartilage sarcoma of nose, thyroid, liver, keloid, angioma, freckle |
| Matsushima et al. | Skin, breast, lung, gland |
| Song et al. | Skin, malignant melanoma, lip, tongue, upper jaw parotid, breast, vagina, penis, osteogenic sarcoma, fibrosarcoma metastatic lymph node |
| Lao et al. | Liver (hepatocellular carcinoma, cholangiocellular carcinoma, mixed hepatocholangiocellular cancer, transparent liver cancer) |
| Quan | Soft tissue sarcoma, head/neck cancer, malignant melanoma, skin cancer, breast cancer, recurrent cancer, metastatic cancer |
| Wang | Liver |

Animal Results

Yokoyama et al. used direct current in canine malignant cancer tissue and found that cancer tissues of 2 cm. in diameter around the electrode became necrotic in 60 minutes. Bleomycin was then injected intravenously and was found to accumulate around the electrode in the majority of cases. Li et al. studied the mechanisms of ECT in normal dog liver and verified that the cell metabolism and its environment are destroyed in agreement with previous theory. Chen et al. studied ECT in mice and verified much of the theory, including the conclusions that tumor cells are more sensitive to changes of their microenvironment than are normal cells and that ECT stimulates the immune system, pointing out that, at an electrode voltage as low as 100 mV, leukocytes concentrate at the anode and lymphocyte antitumor response might be activated. Li et al., like Xin, placed both an anode and a cathode in the tumor. Chou et al. investigated ECT in mice and rats. Pointing out that constant voltage is used in clinics to prevent pain, they used a constant-voltage mode. They also cite the observations of Xin that untreated tumors sometimes disappear after ECT of the primary tumor. The hypothesis proposed to explain this was that is the immune system was enhanced by ECT.

Electroporation

Another electrical therapy that has been attempted for the treatment of cancer is electroporation. This is based on the effective high voltage shocks which temporarily open pores in the cell membranes. This is normally considered a negative byproduct of shocks and is a negative side effect of, for example, defibrillation therapy. The application of a high voltage shock with fields on the order of hundreds of volts per. centimeter will raise the transmembrane potential of the cell above 500 mV. This is over five times the normal activation potential swing of a cell and causes micro-pores to be temporarily open. If opened too long the pores are permanently damaged. The effect of this electroporation is a dramatic increase in the molecular exchange between the inside and outside of the cell.

Electroporation has primarily been used as a research tool and been evaluated for assistance in injecting various drugs, genetic material, proteins, and other substances into cells. Okino et al. used electroporation therapy and a cancer drug in an animal study.

Orlowski et al. also published another use of electroporation (he referred to it as electropermeabilization) of culture cells to increase the effectiveness of anti-cancer drugs.

Belehradek et al. and Hoffmann et al have both reported on the use of electroporation specifically to increase the efficacy of bleomycin respectively in animals and humans.

There have been several patents discussing electrical treatment for cancer. These are primarily due to Nordenstrom as discussed here. All of these systems have been external instruments and there is no discussion or hint that the inventors here are aware of or conceived of a fully implantable or even a battery operated system.

Nordenstrom et al. patented an instrument for destroying a neoplasm in 1981. An instrument external to the body provides direct current and integrates it to determine charge. Electrodes are placed in the body, one in the neoplasm and one a distance away from it. The instrument controls the maximum voltage and current and can interrupt the current when the calculated charge reaches a predetermined value. In another patent granted to Nordenstrom in 1990 his concern was with a physiological way of healing, growing, or modifying tissue by applying a time-varying voltage. The voltage is a damped sine wave or a similar shape, each half cycle of the sine wave adjustably ranging from 0.1 to 10 days. The system can sense the direction of physiological healing and adjust the polarity of the voltage phase to complement it. In practice this is a system that appears to be used long-term but is not described as implantable except for the electrodes. The patent mentions the possibility of a rechargeable power source, programming of the controller, and automatic shutoff. D. Fontaine et al. patented a device reminiscent of an ablation device in 1996. It is of interest in that it includes a catheter tube containing electrodes as well as a lumen for the flow of electrolyte fluid to match the impedance of the tissue to the energy source. This is one example of catheters having electrodes as well as the ability to deliver fluids. B. Nordenstrom et al. patented another in 1986 for treatment of tumors. The patent discusses its advantages in positioning and retention of the electrode, in overcoming problems of gas formation and dehydration at the tumor, and the problem of material deposition on the electrode surface. The control instrument is specified as outside the body. Examples of fluids that can be delivered are cited as sodium chloride solution to increase the conductivity of the tumor as well as cell poison. Another patent to Nordenstrom in 1990 concerns a temporary electrode device suitable for the tumor destruction application. It was designed for ease of entry and removal and has an adjustable length electrode to adapt to different size tumors. P. Eggers et al. received a patent in 1997 for an instrument and a probe with two electrodes to sense whether tissue is normal or tumorous and, in the latter case, benign or malignant. Methods cited include measurement of impedance or dielectric constant. It also includes treatment of the tissue mass to effect necrosis, preferably via heat to cause cauterization. The device is specifically intended for use over a brief period of time.

There have been several patents dealing with the use of electroporation to inject substances into cells. For example Calvin teaches the use of electroporation to introduce DNA while Hoffmann teaches several variations on this theme.

All of the patented art deals with either fully or largely external systems. This ranges from patches around the neck to external power sources into temporarily introduced needles and catheters. These all require use of a catheterization laboratory with all of the attendant costs and personnel, or could be conceivably used with a risk of infection with leads being left in the body and crossing the skin barrier.

With the possible exception of the painful high voltage shocks of electroporation therapy, it appears that the optimal electrocancer therapy obtains from long-term application of low voltages. This would seem to suggest that a battery operated implantable device would be optimal. However, this had not been taught in the literature. The closest are some semi-implantable systems such as an implantable RF Heater of Doss which has a coil inside the body which picks up a very high powered magnetic transmission and converts the heat. Similarly, Hofinann (U.S. Pat. No. 5,501,662) teaches a partially implanted system in which electrodes are left in a blood vessel to shock blood cells, receiving its power from an induction coil again from a high powered outside source. Neither of these is suitable for chronic care.

Thus, in spite of the evidence beginning to accumulate demonstrating the usefulness of some types of cancer electrical therapy, there has been no teaching by a practical implantable device. Such a device could cost effectively and safely deliver cancer therapy without the risk of infection from repeated introduction of needles and catheters into the body.

Also, the use of a system that would use all levels of electrical therapy for cancer treatment has not been taught even on an external basis.

DETAILED DESCRIPTION OF THE DRAWINGS AND PREFERRED EMBODIMENT

Figure 2:
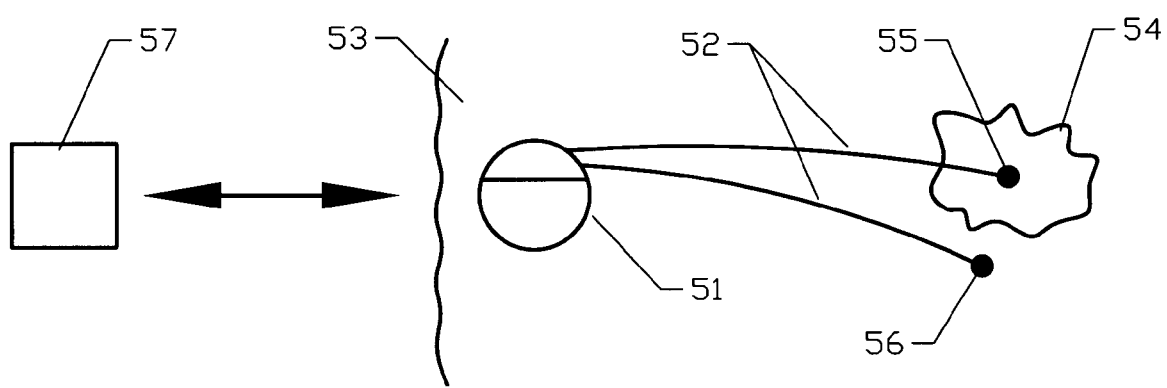
FIG. 2 shows the overall system of the invention.

The system for cancer therapy consists of a body implanted generator 51 and one or more implanted wires or leads 52 as shown in FIG. 2. The generator and leads are implanted in body 53, generator 51 in a convenient subcutaneous area as near as practical to tumor 54 but out of the path of any planned ionizing radiation and leads 55 and 56 are implanted in or outside tumor 54. Anode electrode 55 is typically implanted in the center of tumor 54 and cathode electrode 56 is typically located either outside tumor 54 or on its internal periphery. Leads are tunneled subcutaneously from generator 51 to tumor 54. The lead containing electrode 56 can alternatively be introduced into a blood vessel and be placed in a location near the tumor 54. The system also consists of an instrument 57 used to communicate with the generator.

The system has both similarities and differences from implantable pacemaker systems. Among the differences are:

Duration of implant is typically months, not years.

The system is non life-supporting.

The generator, by virtue of its expected longevity, has lower hermeticity requirements.

The leads have less stringent mechanical requirements since they are not stressed by movement to as great a degree and since they have a shorter required longevity.

Lack of concern for electromagnetic interference.

Other differences and unique features will be discussed below. It should be mentioned that the complexity of the device can vary considerably, depending upon its desired flexibility of use. In the simplest case it can consist of a single lead permanently connected to a generator encapsulated in a plastic or potting compound with a fixed DC output voltage and no external instrument for communication and control. However, this discussion will range over the entire scope of options possible for this system.

1. Leads

FIG. 3 shows options for the lead system. In FIG. 3a a unipolar lead 60 has one electrode 61 implanted in or adjacent a tumor 62. The generator 63 serves as the reference electrode. In FIG. 3b multipolar lead 70 has 2 or more electrodes 71, 72 implanted in or adjacent a tumor 73. Electrode 71 would serve as the anode and 72 would serve as cathode or vice versa. In FIG. 3c lead 80 has one or more electrodes 81 implanted adjacent tumor 82 and lead 83 has one or more electrodes 84 implanted adjacent tumor 82. A variation of FIG. 3c is represented by FIG. 2 in which the anode electrode 55 is implanted within tumor 54. Many variations are possible. The goal is to establish an electric field encompassing as much of the tumor as possible and as little of the surrounding area as possible. FIG. 3d shows three leads 90–92. Electrodes 93 and 94 are anodes and electrodes 95–98 are cathodes. Alternatively, two separate circuits can be established with electrodes 93, 95 and 97 forming one and electrodes 94, 96, and 98 forming the other. The leads may be permanently connected to the generator or may be attached with a releasable mechanism, depending upon the desired cost vs. system flexibility. For example, the low cost system would employ leads of fixed length and means of anchoring to the tissue. Those leads would not be removable from the generator. Lead and electrode material may be of the kind used in implantable pacemakers, i.e., inert metals such as platinum but generally without the need for sophisticated non-polarizable electrodes. The major stress will be placed upon the leads during implantation and their strength should be a compromise between reducing the diameter and being able to withstand kinking during implant. A few strands of platinum iridium coated with insulation should suffice per electrode. A lumen or stylet aperture is optional.

Figure 3A:
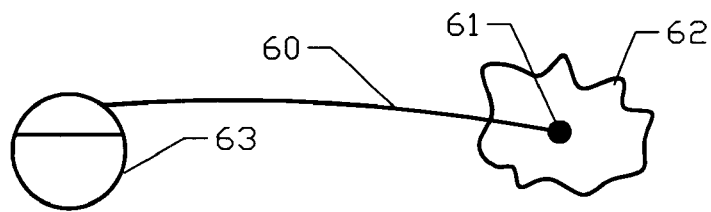
FIG. 3 shows the lead placements of the invention.
Figure 3B:
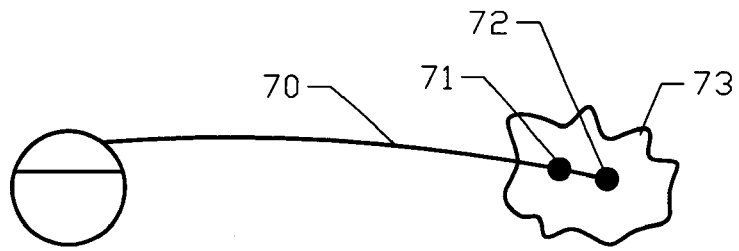
Figure 3C:
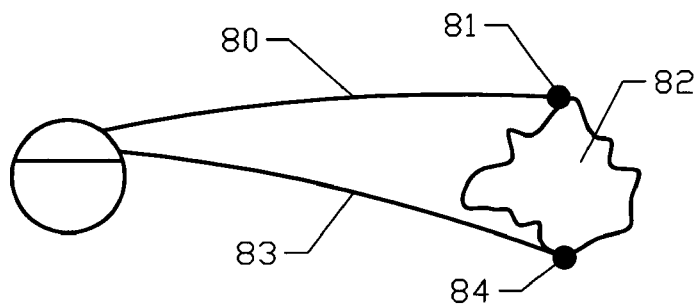
Figure 3D:
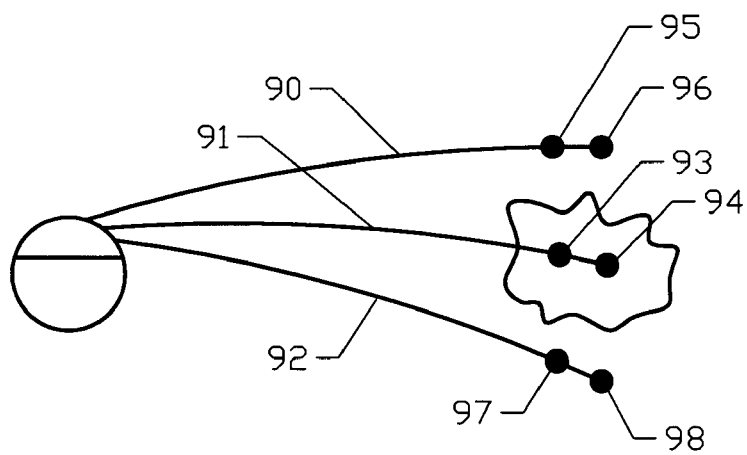
Figure 3E:
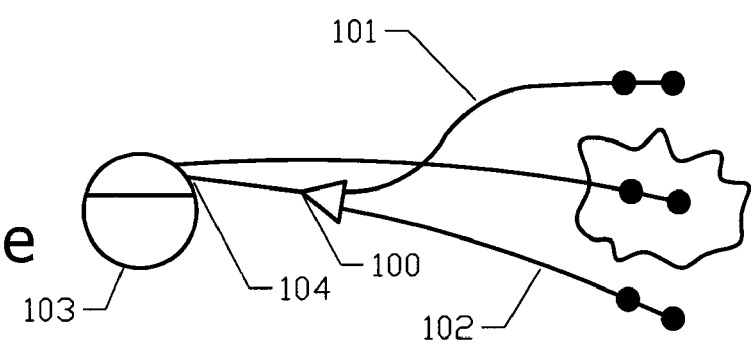

Leads may be supplied in various lengths or in a single length, with excess lead being wrapped around the generator in its body "pocket." The system may provide lead adaptors to permit the use of additional leads for larger tumors as illustrated in FIG. 3e in which lead adapter 100 allows leads 101 and 102 to enter generator 103 electrically at the same location 104. The most complex and costly lead designs contain sensors (as described below).

Figure 4A:
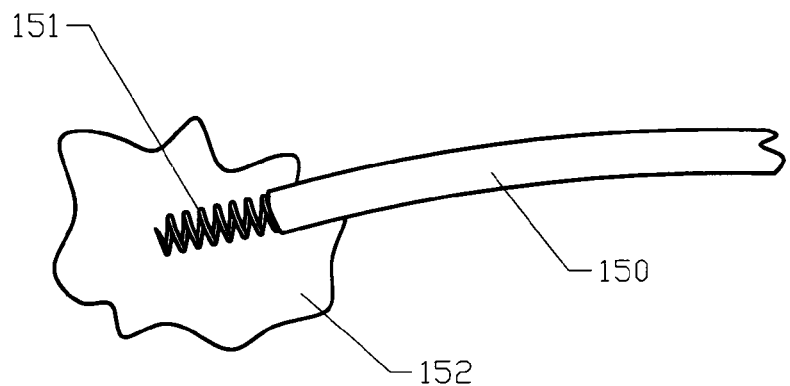
FIG. 4 shows the lead systems of the invention.
Figure 4B:
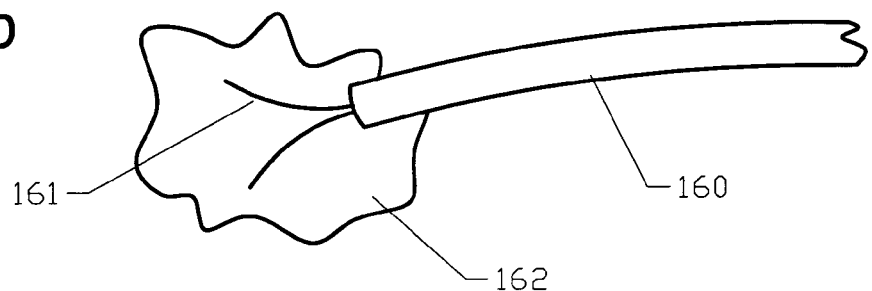
Figure 4C:
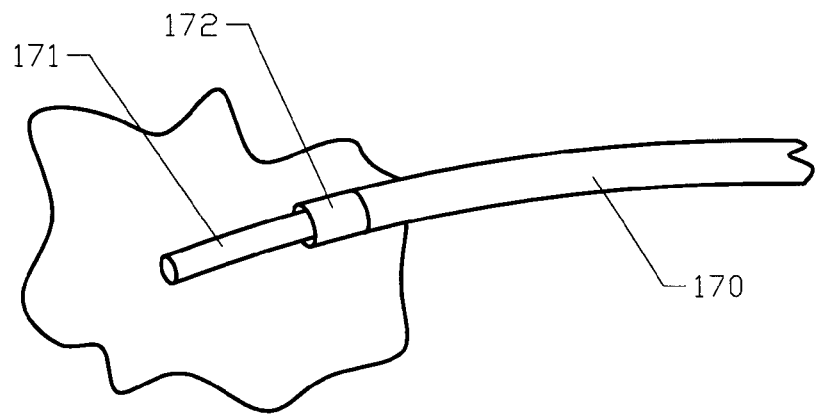

The lead anchoring mechanism represents an important consideration. It is generally anchored in tissue quite different from heart muscle, typically softer. The anchoring mechanism must permit penetration of the tissue, anchoring in soft and retracting tissue, and safe removal. FIG. 4 shows several possibilities. FIG. 4a shows a screw-in lead 150 having a screw 151 designed to be left within the tumor 152 during therapy. In FIG. 4b lead 160 features 2 or more prongs 161 which expand into tumor 162 and are left expanded during therapy. The anchoring for the leads of these devices is more akin to so-called active fixation pacing leads than to passive fixation leads. The mechanisms in FIG. 4 may or may not be used as electrodes as well as anchoring means. Ideally, lead design would be specific to the type, size and location of the tumor. FIG. 4c shows a lead 170 having two or more overlapping telescoping cylindrical electrode sections 171, 172 which may be adjusted either pre- or post-implantation to an optimum length. In the figure electrode section 171 has been extended from electrode section 172.

2. Generator

Figure 5:
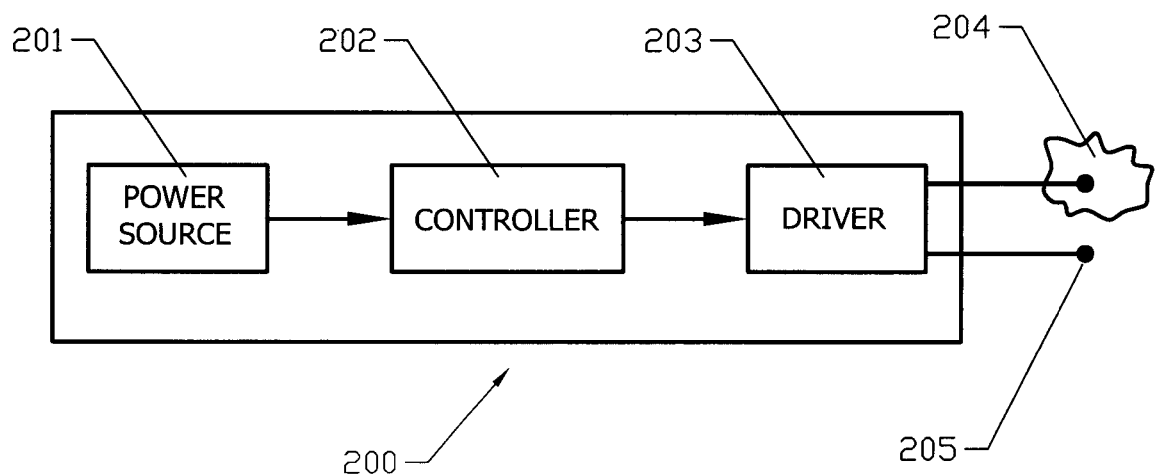
FIG. 5 shows the basic generator of the invention.

FIG. 5 shows a block diagram of the most fundamental generator 200. The power source 201 may be a primary battery, a rechargeable battery, or a receiver of RF energy coupled from outside the body. In the preferred embodiment battery voltage is available to driver circuit 203 which provides DC current to the lead electrodes 204, 205. Controller 202 permits the voltage to be turned on or off by the patient or physician and may consist of a magnetic reed switch activated by an external permanent magnet. Driver circuit 203 delivers regulated voltage or constant current to the electrodes to compensate for changes in impedance seen at the electrodes.

Figure 6:
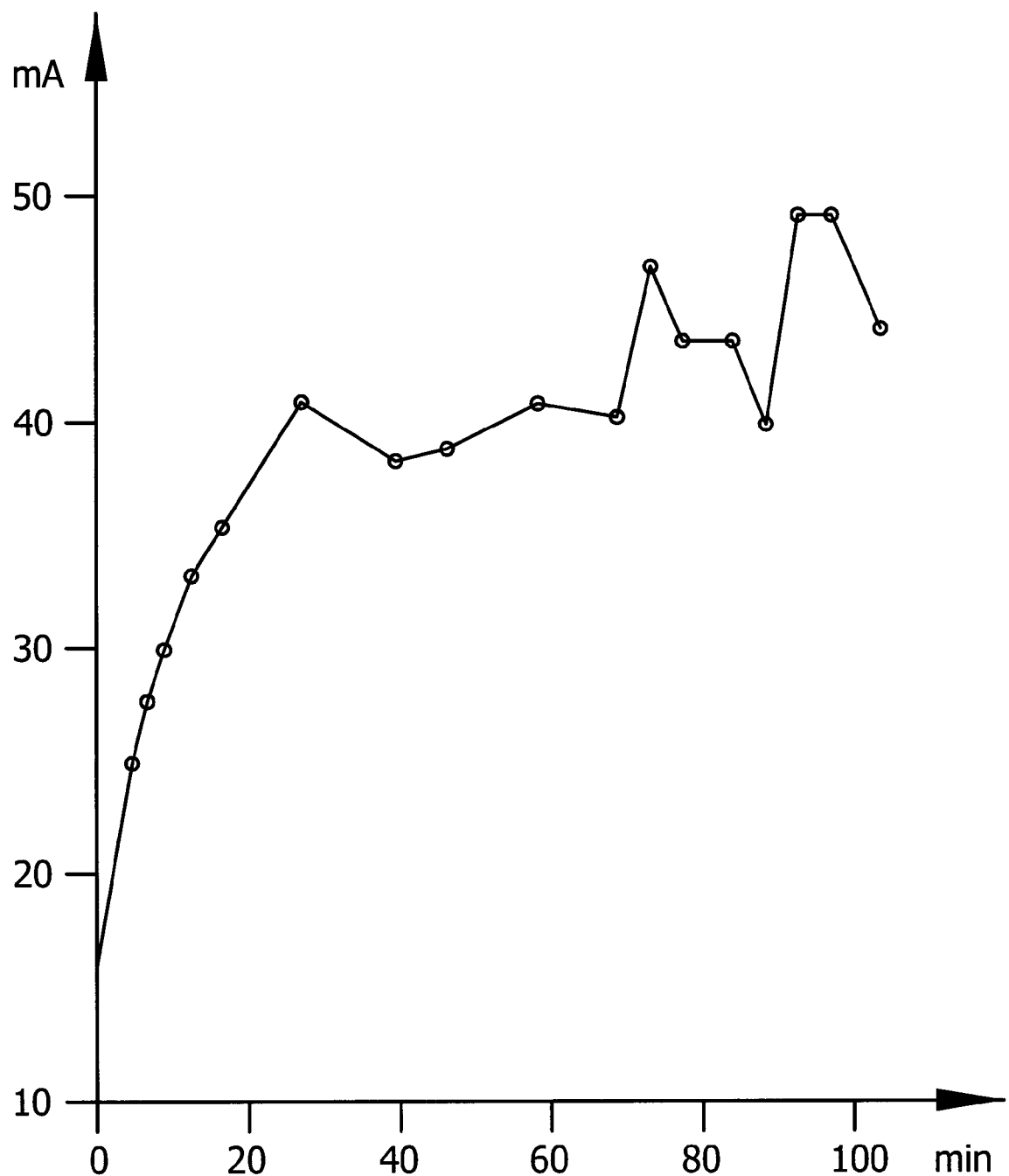
FIG. 6 is a graph of current vs. time for treatment of a pulmonary tumor.

FIG. 6 is a graph of current in mA vs. time for treatment of a pulmonary tumor taken from Nordenstrom. The voltage was 10 V and 250 coulombs were delivered. In the implantable device, the same number of coulombs can be delivered at 50 microamperes if supplied for 100,000 minutes, or 69.4 days. Alternatively, the generator can deliver 10 microamperes at 10 V for 347 days. This represents a practical device. Perhaps a more attractive device would operate at 8 V and deliver 20 microamperes for one year. This would deliver about 500 coulombs and would, in the light of present clinical experience, be usable for most tumors.

A typical Lithium Iodide cell has an output impedance on the order of 1 KΩ and thus is limited to providing an average current of under 1 mA. The above current profiles could be easily provided. However, a carbon monofluoride cell has much lower output impedance and is more suitable for generating EPT shocks. The implantable device may contain multiple power sources, each suitable for a different therapy. For example, one might use a rechargeable cell for higher current applications.

Figure 7:
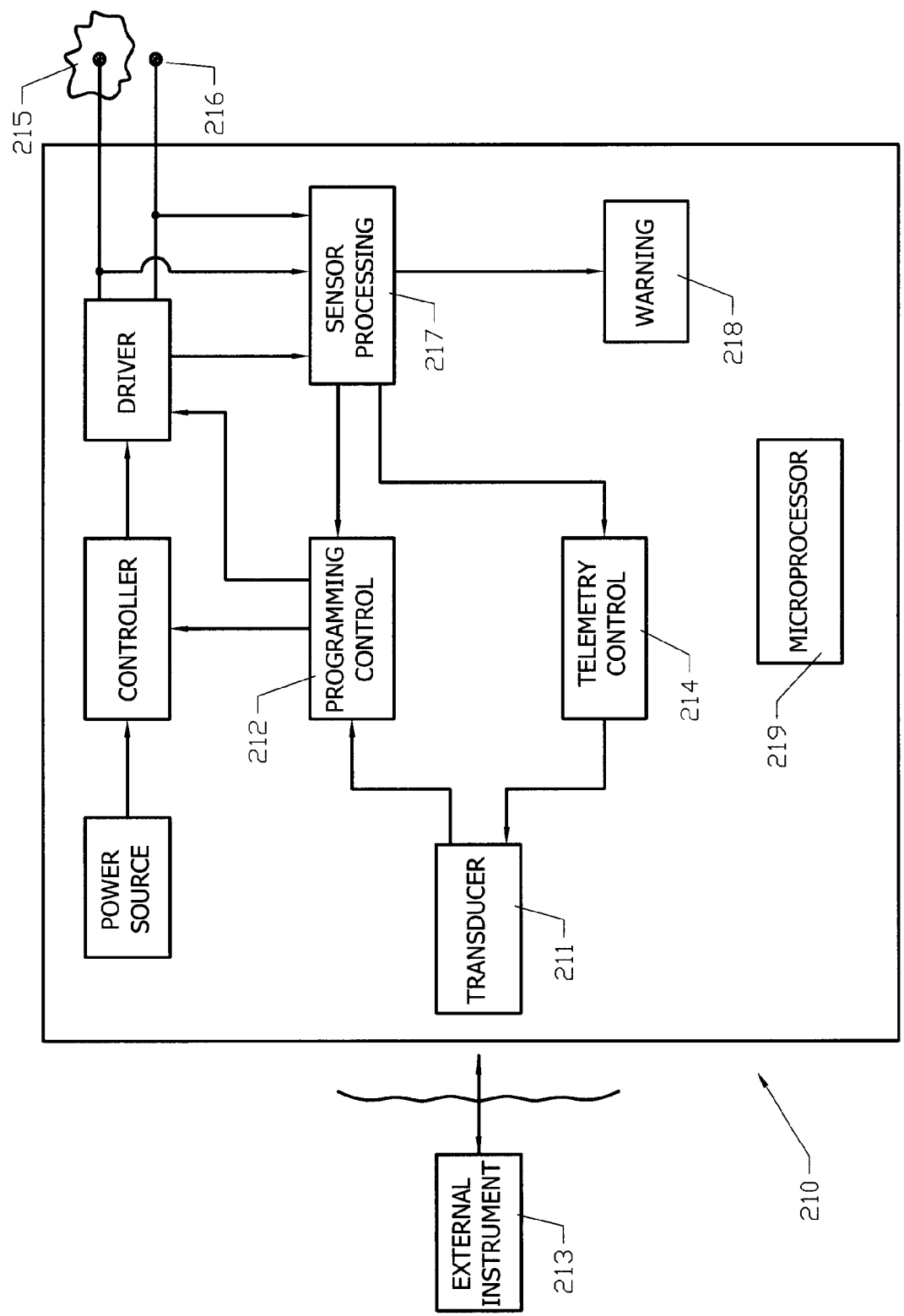
FIG. 7 shows the advanced generator of the invention.

FIG. 7 shows an enhanced block diagram of generator 210 in which several parameters can be programmed, including voltage or current amplitude and output polarity (to switch anodes and cathodes). It may also allow programming the total number of coulombs to be delivered to the electrodes. This is accomplished via transducer 211 and controller 212 using commands transmitted by external instrument 213. Telemetry circuit 214 allows information to be transmitted to the external instrument 213 from the generator 210. This includes battery status (e.g., remaining life), coulombs delivered, and information sensed from the tumor via the electrodes 215, 216 or via special sensors. The sensed information supplies tumor size, density, or chemistry data. For example, pH may be measured at the tumor. Other embodiments include a measurement of pressure as the tumor shrinks or grows, an index of tumor proliferation, or an electrode displacement indication. These may be accomplished via physical sensors such as measurement of electrode/tumor impedance, pressure measurement, or optical sensing or by chemical sensors. Note that chemical sensors are more practical for use in this device than in implanted pacemakers because of the shorter duration of the implant and thus the lower sensor stability requirements.

The electrode device may contain a thermocouple or thermistor to sense heating of the tumor environment as a measure of safety and degree of necrosis. Sensors will be designed to be exposed to ionizing radiation if radiation therapy is probable. Sensed information is processed at signal processor 217 and can be telemetered 214 to external instrument 213 via transducer 211 and/or can be used to control the generator directly. For example, sensing of excessive heating or gas buildup can cause the therapy to be stopped until the tissue cools or the gas is resorbed. Other features of the generator may include defibrillation protection, a controller that gradually increases voltage at the start of the treatment, a programmable timer to control duration of therapy or sequence of therapy, and a warning signal 218 (e.g., audible or vibration) to the patient to signal battery depletion, open or short circuit or other conditions warranting attention. The entire device is preferably under control of a microprocessor 219, although its simplicity may not require computer control. Driver 220 may have several sections, each suitable for a different therapy depending on the voltage and current levels required. Portions of the entire device may be operated in a "sleep" mode to conserve energy when not in use.

Signal processor 217 is preferably a DC amplifier which would detect the intrinsic body "healing" currents being generated to run to the tumor. The generator can begin the process by "priming the pump" with a short duration DC current which should help the body initiate its own therapeutic currents. Output current levels may be either programmed or adjusted automatically to optimum levels to minimize tumor cell proliferation.

Although electrical stimulation alone has been shown to be effective, it has most often been used in conjunction with chemotherapy or radiation therapy. Periodic chemotherapy may be applied by traditional means independent of the implant. Alternatively, the implant may be designed to supply the chemotherapy as well as the electrical stimulation. In a first embodiment of this concept the generator contains a subcutaneous port for penetration by a hypodermic needle. The drug is infused in real time through the port and through a delivery tube into the tumor. The delivery tube may be built into the lead or it may be a separate tube. In the second embodiment, the generator contains a reservoir for storage of the drug. Under control of a timing circuit the drug is released through a tube into the tumor. The technology of implantable drug infusion pumps, ports, and tubes is well known.

In the discussion that follows, the electrical therapy is described as being the application of voltages. The therapy could just as well be described in terms of currents by application of the famous Ohm's law which states that the voltage and current are proportional. Of course, this proportionality constant is the resistance in the electrode/tissue system. Because of changing resistances with long term DC electrical therapy, some physicians may choose to program the devices in terms of current instead of voltage.

Thus, while the following discussion and claims are rendered in terms of voltages, they should be considered to also refer to the appropriate currents.

Figure 8:
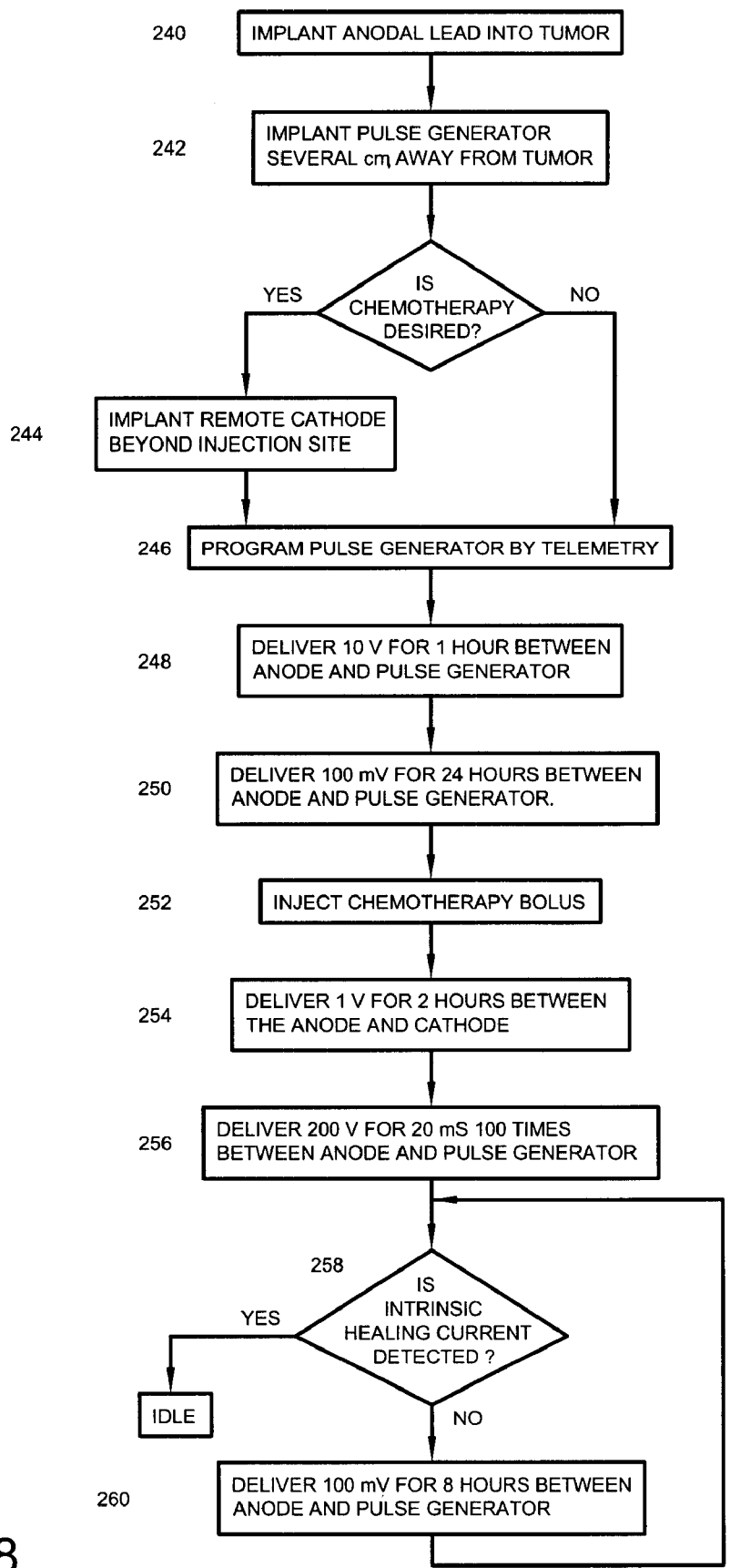
FIG. 8 shows the method of the invention.

FIG. 8 shows the basic method of the invention. First at step 240 the anodal lead is implanted into the tumor. At step 242 the pulse generator is implanted at least several centimeters away from the tumor. If adjunctive chemotherapy is desired then the remote cathode is also implanted at step 244 beyond the injection site or somewhat out of the direct path from the tumor to the injection site. The remote cathode could be left in a large vein. The pulse generator is programmed by telemetry at step 246.

The following electrical parameters are all programmable by the physician and thus should only be seen as illustrative. The first electrical therapy 248 is the supply of 10 volts between the anodal electrode and the generator housing for a period of 1 hour. This will change the pH in the tumor and begin rapid destruction. A voltage between 1 and 20 V is practical for this function. Durations between 10 minutes and 1 day are useful for this application.

Then a low voltage field of 100 mV is applied at step 250 for 1 day between the anodal electrode and the housing. This provides leukocytes (white cells) to the tumor to begin cleaning up the aftermath of the initial destruction. Note that these durations are not attainable with pacemakers (which typically generate 1 mJ pulses). A 100 mV voltage for one day with a system impedance of 1000 Ω requires nearly 1000 times as much energy (864 mJ). This voltage should be high enough to attract the white cells but below the electrolysis level as the high levels of oxygen are not desired at this point. Voltages between 20 mV and 500 mV are appropriate. Durations in the range of 1 hour and 1 week are useful for this function.

At step 252 the chemotherapy bolus is injected. At step 254 the generator to produces a field of 1 V for preferably 1 to 30 minutes (although the circuitry would allow up to 2 hours) between the anode and the remote cathode to attract the chemotherapeutic agent to the tumor. The polarity at the tumor depends on the net charge of the dissolved chemotherapy drug, e.g. for a negatively charged drug, the tumor electrode polarity would be positive. The amplitude of this voltage can vary from 100 mV up to about 10 V although the 1 V range is preferred for energy conservation reasons.

At step 256 the generator produces a large field of 200 V for 10 ms pulses 100 times (with 10 ms spacing in between) between the anode and the remote cathode to force open the cancer cell membranes (electroporation) to facilitate the entry of the large drug molecules into the cancer cells. The use of a smaller field from 20 V pulses would be of utility but would not require as much energy usage and battery capacity. Voltages up to 900 V would be even more beneficial and are practical to generate in an implantable device. Pulse widths in the range of 100 μs to 20 ms are practical for this particular function. Spacing periods of 100 μs to 1 second are appropriate between the pulses. The repetition of 100 times is only illustrative and repetitions of 1 to 10,000 pulses are useful for this electroporation function. Also, the device gives the physician the option of choosing the device housing as the remote electrode based on the considerations of patient comfort, safety (avoiding cardiac fibrillation), and electroporation effectiveness.

At step 258 the generator begins monitoring the voltage between the anode and the pulse generator housing. If an intrinsic healing current is detected then no further therapy is provided until the device is reprogrammed and the system sits in idle mode of step 260. If no healing current is detected then the system will provide a field of 100 mV between the anode and the generator housing in step 262 until turned off. Voltages between 20 mV and 500 mV are appropriate. Durations in the range of 1 hour and 1 month are useful for this healing current function.

Figure 9:
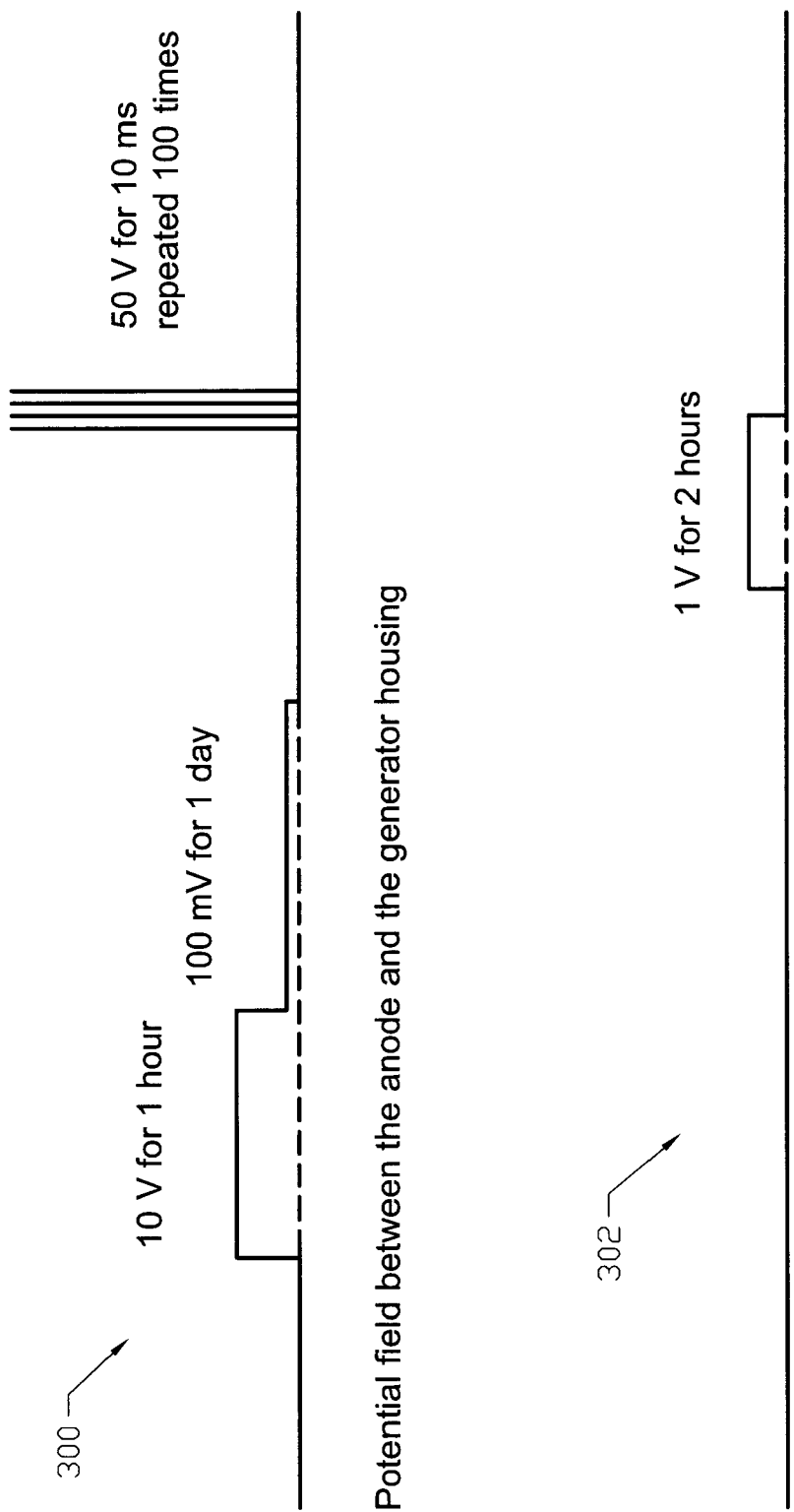
FIG. 9 shows the voltage profiles of the invention.

FIG. 9 shows the voltage profiles of the invention as described under the method above. Profile 300 is that between the anode and the housing while profile 302 is that between the anode and the remote cathode.

Figure 10:
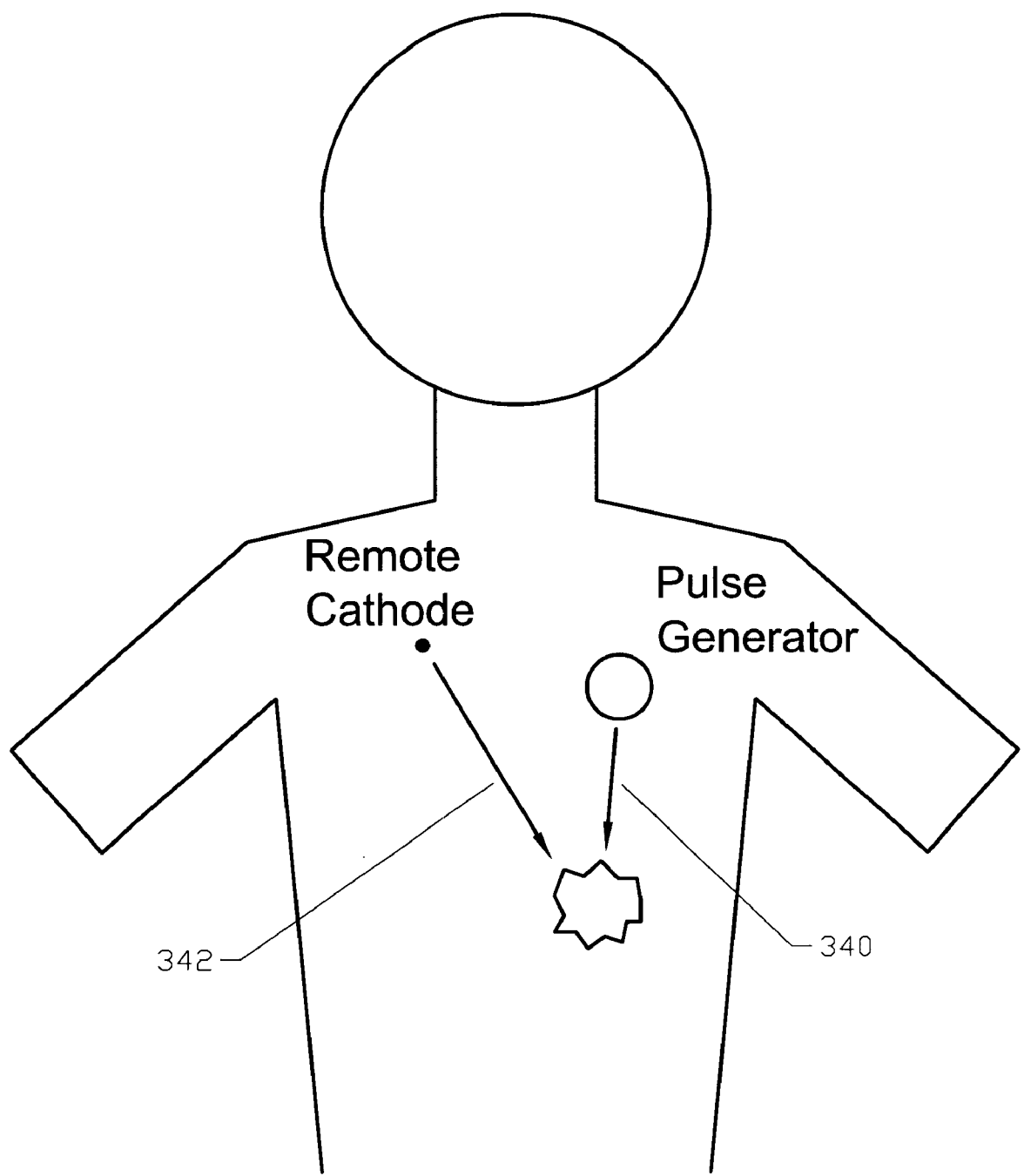
FIG. 10 shows the generator housing being used as an electrode.
Figure 11A:
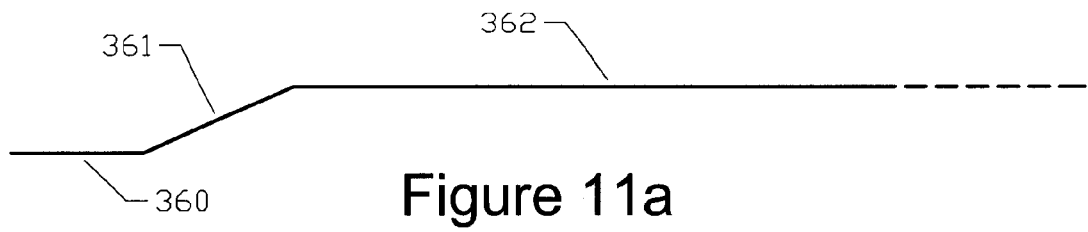
FIG. 11 shows other electrical profiles useful in this invention.
Figure 11B:
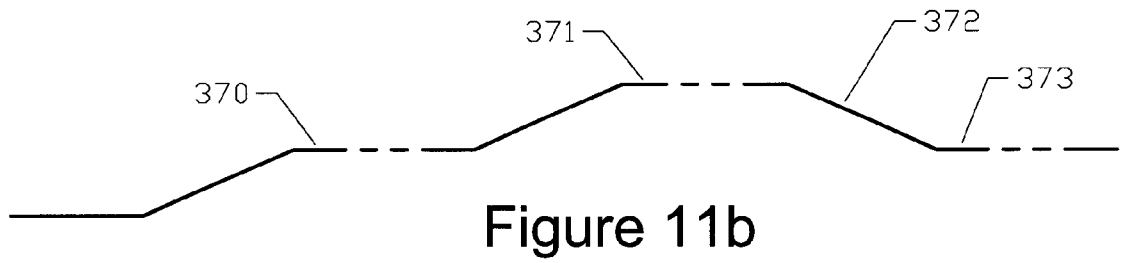
Figure 11C:
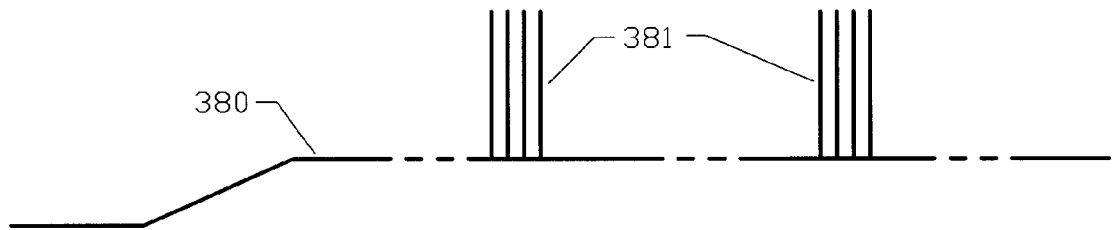
Figure 11D:
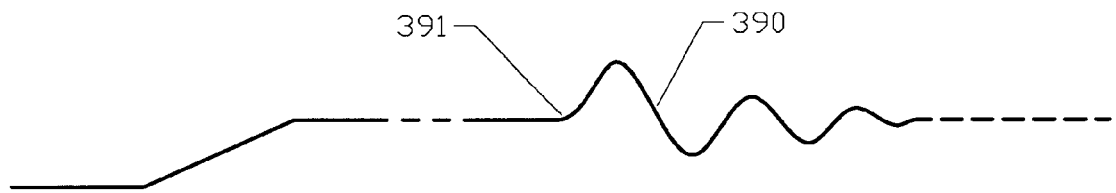

FIG. 10 shows the body current paths. Note the primary therapeutic current 340 is between the anode (in the tumor) and the pulse generator housing as the cathode. The secondary current 342 is between the anode and the remote cathode. Preferably, the generator is located near the tumor and is the cathode for all currents except for the chemotherapy electrophoresis. In that case, one desires to have a remote cathode far away to better direct the intravenous drugs to the anode. This is the secondary current 342.

FIG. 11 shows other possible variations in current levels for this therapy. In FIG. 11*a* the therapeutic current level 362 is attained by gradually increasing the current 361 from the initial baseline 360. In FIG. 11*b* therapeutic current 370 is increased to level 371 in response to an input from the microprocessor and later restored gradually 372 to its original value 373. These changes may be in response to a sensor input, to circadian or other body rhythms, or to a change in measured heart rate variability. FIG. 11*c* shows a therapeutic current level 380 and multiple electroporation therapies 381 applied at desired times, perhaps corresponding to chemotherapy sessions.

Figure 1:
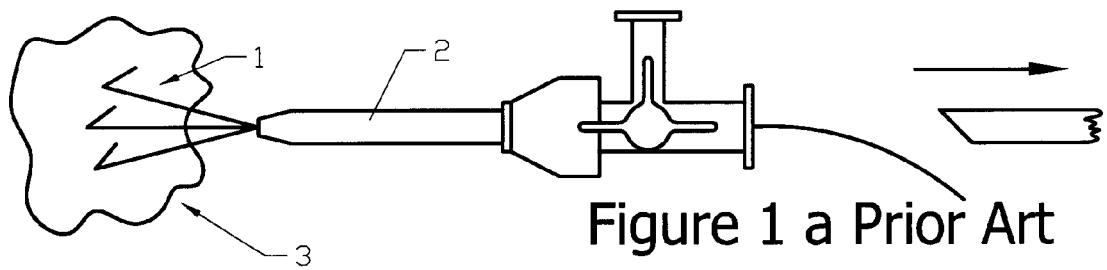
FIG. 1 shows leads that have been used in acute research studies.
Figure 1:
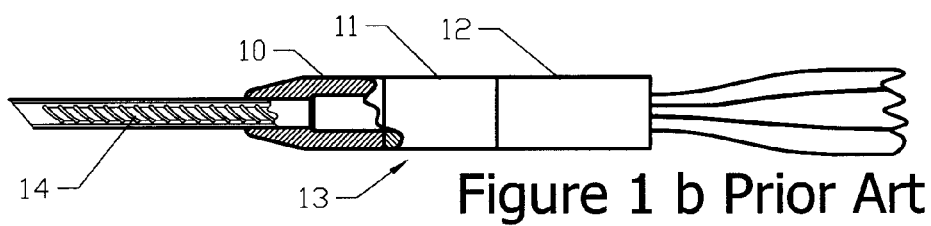
Figure 1:
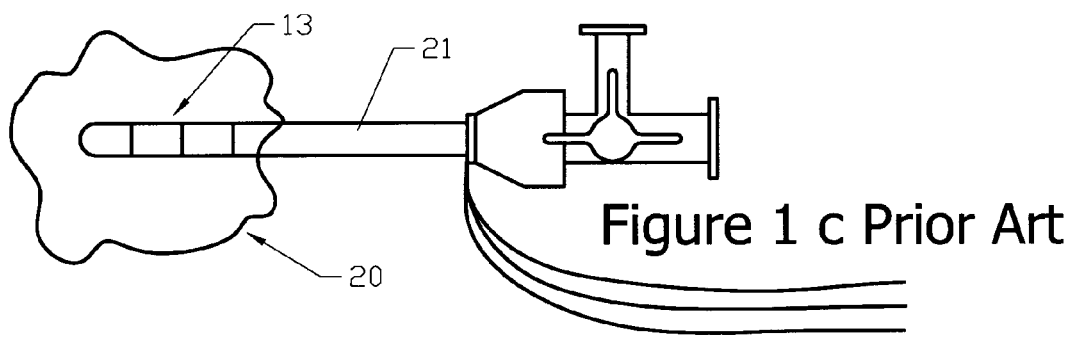
Figure 1:
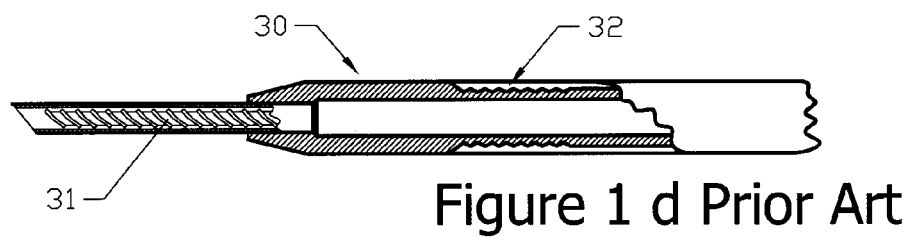
Figure 1:
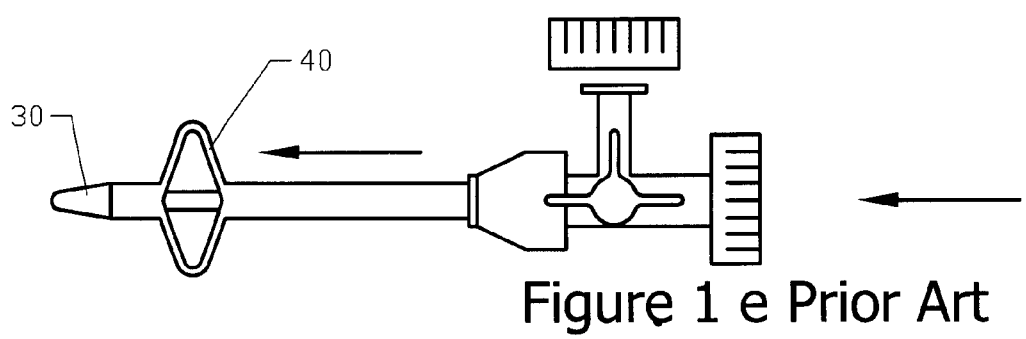

The electroporation pulses may be biphasic and may be applied synchronously with a detected heartbeat in order to reduce the risk of inducing cardiac arrhythmias. Feedback may also be used to adjust electroporation parameters. For example, the electrical consequences of electroporation may be used to adjust the distribution of the electrical field at the electrodes. FIG. 1*d* shows the use of electrochemical therapy with a healing signal 390 generated within the implantable device. After it has been determined that the tumor has been destroyed, at the time designated at 391, the device applies a healing current to the former tumor site.

The implantable device may be used in conjunction with radiation and chemotherapy. By employing it over a long time period it helps kill some malignant cells that have developed resistance to radiation or to anticancer drugs. The implant can be used to aid in gene transfer therapy and electroimmunotherapy as well as in conjunction with vasoconstriction drugs. It can be used with hyperthermia, ultrasonics, and magnetotherpay as well.

As an alternative embodiment, the device can be programmed to await a command from the patient to begin any stage of the electrical therapy.

Figure 12:
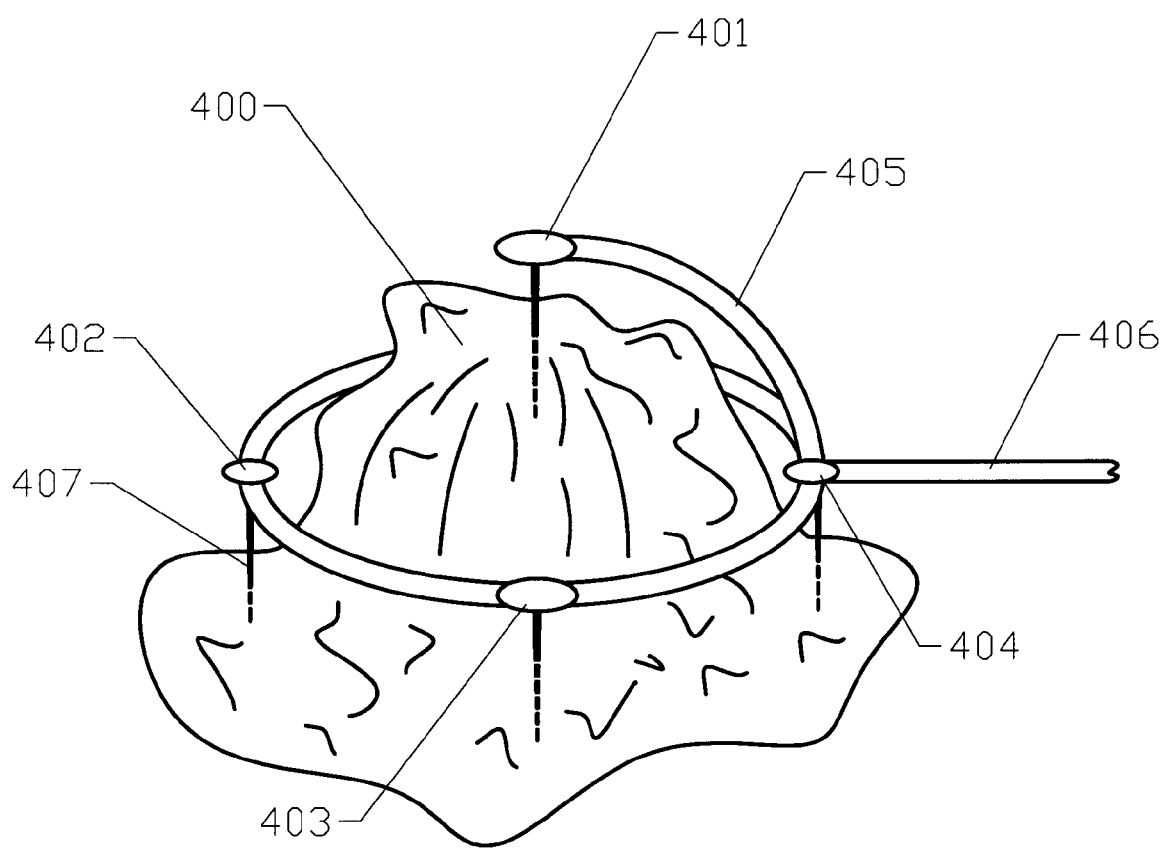
FIG. 12 shows a tumor to which 5 electrodes have been applied in an array.

Electrode arrays can be particularly important in increasing the effectiveness of electroporation therapy. They work to establish an electric field pattern that encompasses all of the tumor volume. FIG. 12 shows a tumor 400 to which 5 electrodes have been applied in an array. Four of the electrodes are shown in the figure. Electrode 401 is affixed to the top of the tumor and electrodes 402, 403, and 404 encircle the tumor. Electrode 401 is electrically connected to wire bundle 406 via insulated wire 405. Each of the other four electrodes is individually connected to bundle 406 in similar fashion. Wires 406 are attached to the generator package. Each electrode is fixed to tissue via a needle such as 407 which may or may not be part of the electrode. This array can be used for both electrochemotherapy or electroporation.

Current paths can be switched by the implantable generator so that, for example, a current pulse can flow from 404 to 401, then from 403 to 401, then from 402 to 401, etc. in any desired sequence. Two or more electrodes may simultaneously be used as anodes or cathodes for DC therapy.

An array similar to that of FIG. 12 is shown schematically in FIGS. 14*b* and *c*. FIG. 14*b* is a top view and FIG. 14*c* is a side view. Only the center electrode 420 has a fixation device such as needle 421. In FIG. 14*a*, the center fixation device is not an electrode. The entire array is contained within a flexible polyurethane (or other polymeric) coating. Electrodes 423–426 rest on the tissue without active fixation. An array with no active fixation is shown in two views in FIG. 13. Electrodes 410–413 encircle the tumor and wire bundle 414 connects to the generator.

Figure 13:
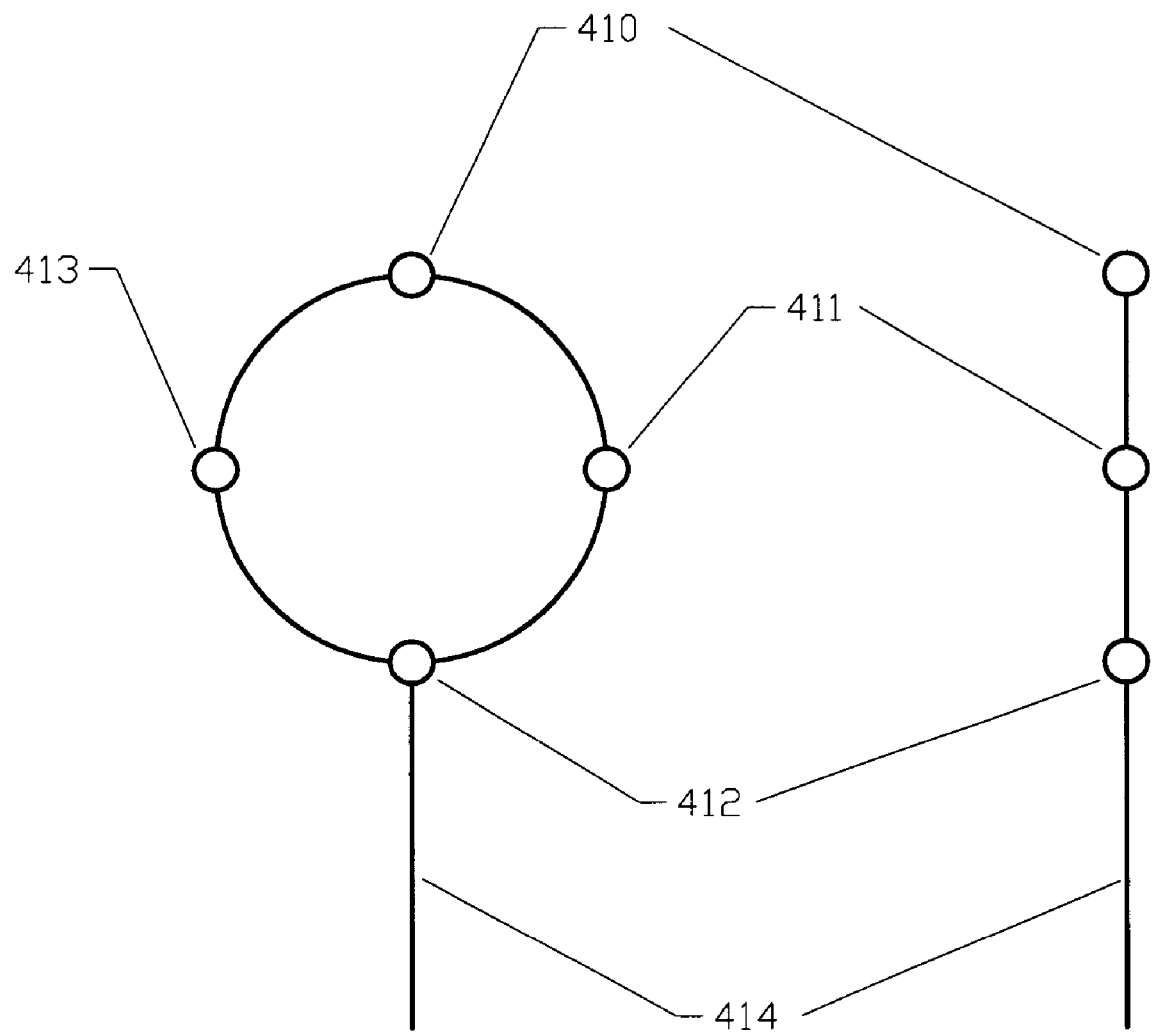
FIGS. 13–16 depict various electrode array embodiments of the invention.
Figure 14:
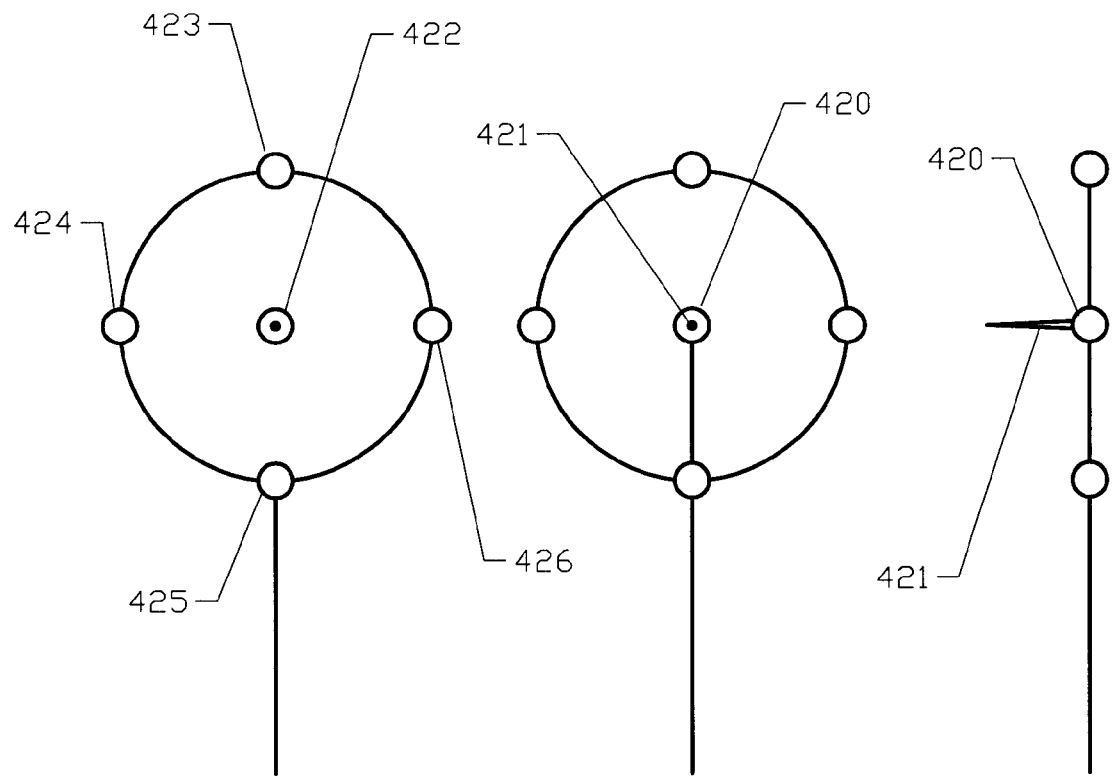
Figure 15:
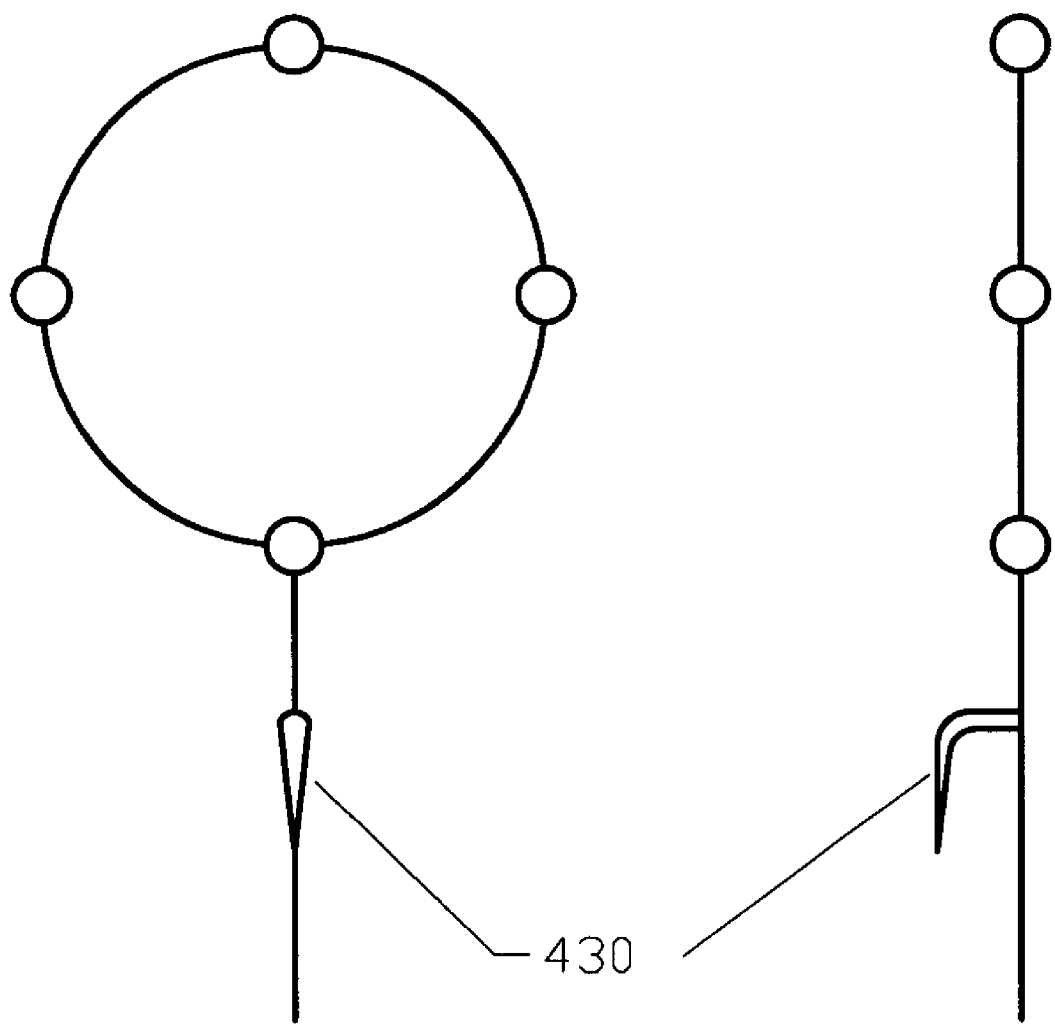

FIG. 15 is similar to FIG. 13 except that it has a fixation hook 430 to hold the array in place.

Figure 16:
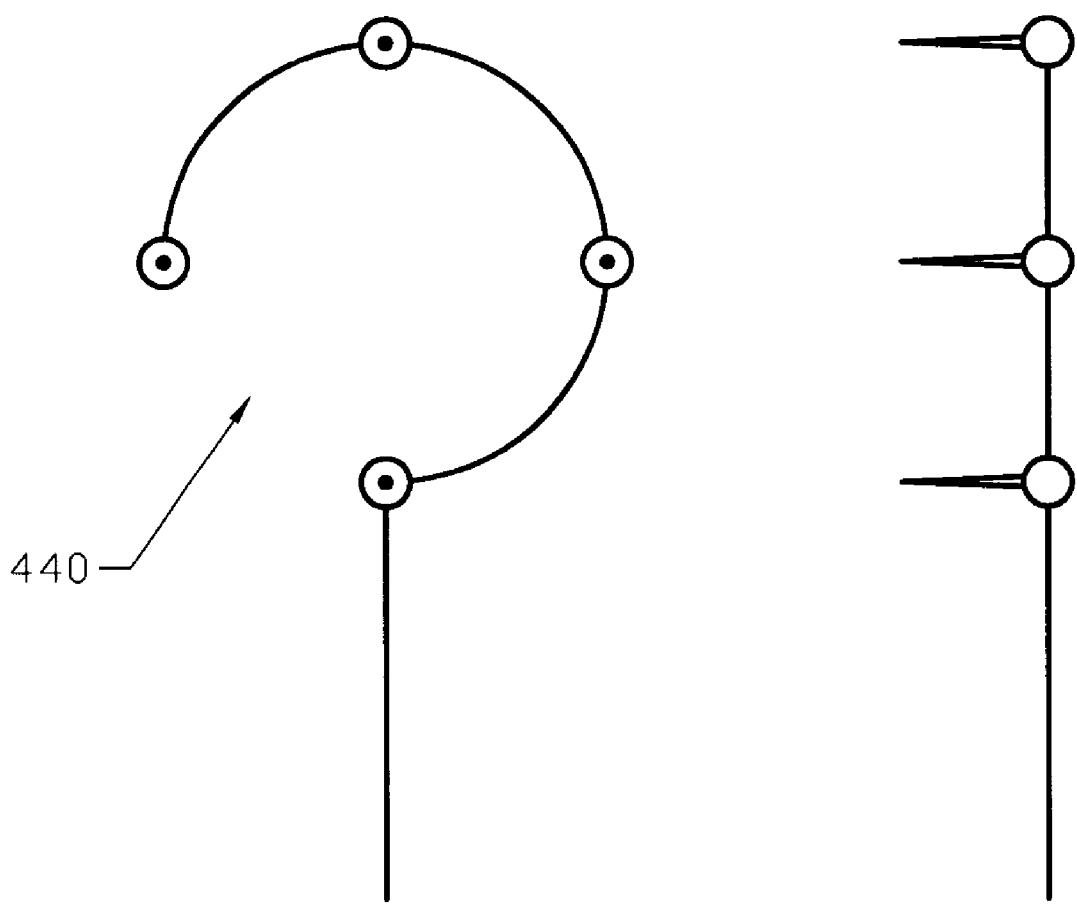

Some practitioners may wish to avoid puncturing the tumor or its immediate periphery. FIG. 16 shows an array in top and side views that, by virtue of opening 440 is flexible and can be fixed around tumors of various shapes and sizes. The number of electrodes and the fixation mechanism are not limited to those shown in FIGS. 12–16. Furthermore, such arrays may also include sensors as well as electrodes.

We claim:

1. A method of treating solid tumor cancers comprising the steps of: (1) implanting at least one electrode into or near a tumor, (2) implanting a source of electrical power, (3) connecting the electrode to the source of electrical power and (4) delivering electrical current into the tumor.

2. The method of claim 1 in which the source of electrical power is implanted several centimeters away from the tumor.

3. The method of claim 1 in which a chemotherapy agent is injected proximate to the timing of the electrical therapy.

4. The method of claim 1 in which the electrical therapy involves the use of multiple voltages.

5. The method of claim 1 in which the electrical therapy delivered by the source of electrical power involves the application of voltages between 1 volt and 20 volts.

6. The method of claim 1 in which the electrical therapy delivered by the source of electrical power involves the application of voltages for a time period of between 1 minute and 1 day.

7. The method of claim 1 in which the electrical therapy delivered by the source of electrical power involves voltages and time periods useful for changing the pH inside a tumor.

8. The method of claim 1 in which the electrical therapy delivered by the source of electrical power involves the application of voltages of between 20 mV and 500 mV.

9. The method of claim 1 in which the electrical therapy delivered by the source of electrical power involves the application of voltages for a time period of between 1 hour and 1 week.

10. The method of claim 1 in which the electrical therapy delivered by the source of electrical power involves voltages and time periods useful for attracting white blood cells.

11. The method of claim 1 in which the electrical therapy delivered by the source of electrical power involves the application of voltages of between 100 mV and 10 V.

12. The method of claim 1 in which the electrical therapy delivered by the source of electrical power involves the application of voltages for a time period of between 1 to 120 minutes.

13. The method of claim 1 in which the electrical therapy delivered by the source of electrical power involves voltages and time periods useful for changing the pH inside a tumor.

14. The method of claim 1 in which the electrical therapy delivered by the source of electrical power also involves the application of voltage pulses of between 20 and 900 volts.

15. The method of claim 1 in which the electrical therapy delivered by the source of electrical power also involves the application of voltage pulses with a pulse width of between 100 $\mu$s and 20 ms.

16. The method of claim 1 in which the electrical therapy delivered by the source of electrical power also involves the application of voltage pulses with a spacing period of between 100 $\mu$s and 1 second.

17. The method of claim 1 in which the electrical therapy delivered by the source of electrical power also involves the application of between 1 and 10,000 voltage pulses.

18. The method of claim 1 in which the electrical therapy delivered by the source of electrical power also involves voltages and pulse widths useful for forcing open tumor cell membranes to better allow the flow of therapeutic substances.

19. A method of treating solid tumor cancers comprising the steps of: (1) implanting at least one electrode into a tumor, (2) implanting a source of electrical power, (3) connecting the electrode to the source of electrical power, (4) monitoring at least one voltage from within tissue, and (5) delivering electrical current into the tumor.

20. The method of claim 19 in which the electrical therapy delivered by the source of electrical power is adjusted according to the sensed tissue voltage.

21. The mothod of claim 19 in which the electrical therapy delivered by the source of electrical power involve voltages in the range of 20 mV to 500 mV.

22. The method of claim 19 in which the electrical therapy delivered by the source of electrical power involve time durations in the range of 1 hour to 1 month.

* * * * *